United States Patent [19]

Newsham et al.

[11] Patent Number: 5,445,854
[45] Date of Patent: Aug. 29, 1995

[54] NONLINEAR OPTICAL EPOXY-CONTAINING COMPOSITIONS AND CROSSLINKED NONLINEAR OPTICAL POLYMERIC COMPOSITION THEREFROM

[75] Inventors: Mark D. Newsham; Muthiah N. Inbasekaran; Michael N. Mang, all of Midland, Mich.

[73] Assignee: The Dow Chemical Company, Midland, Mich.

[21] Appl. No.: 329,374

[22] Filed: Nov. 29, 1993

[51] Int. Cl.$^6$ ............... C08G 59/00; C08G 65/08; C08G 65/14

[52] U.S. Cl. ........................... 428/1; 427/488; 427/491; 525/502; 525/504; 528/96; 528/97; 528/98; 528/99; 528/103; 528/104; 528/107; 528/109; 528/114; 528/116; 528/117; 528/120; 528/123; 528/124; 528/327; 528/407; 528/422

[58] Field of Search ............ 525/502, 504; 528/96, 528/97, 98, 99, 103, 104, 107, 109, 114, 116, 117, 120, 123, 124, 327, 407, 422; 428/1; 427/488, 491

[56] References Cited

U.S. PATENT DOCUMENTS

| | | | |
|---|---|---|---|
| 3,395,329 | 7/1968 | Rentzepis | 321/69 |
| 3,431,484 | 3/1969 | Pao et al. | 321/69 |
| 3,858,124 | 12/1974 | Bass et al. | 332/7.51 |
| 4,994,209 | 2/1991 | Okazaki | 252/587 |
| 5,106,936 | 4/1992 | Gulotty et al. | 528/125 |
| 5,112,934 | 5/1992 | Kester et al. | 528/99 |
| 5,173,546 | 12/1992 | Kester et al. | 525/504 |
| 5,187,237 | 2/1993 | Nordmann et al. | 525/326.2 |
| 5,208,299 | 5/1993 | Bales et al. | 525/437 |
| 5,288,816 | 2/1994 | Inbasekaran et al. | 528/98 |

FOREIGN PATENT DOCUMENTS

| | | |
|---|---|---|
| 0406888A2 | 1/1991 | European Pat. Off. . |
| 0445864A1 | 9/1991 | European Pat. Off. . |
| 0474402A2 | 3/1992 | European Pat. Off. . |
| 920341 | 3/1992 | WIPO . |

OTHER PUBLICATIONS

Swalen et al., "Poled Epoxy Polymers for Optoelectronics", *Organic Molecules for Nonlinear Optics and Photonics*, J. Messier et al. editors, vol. 194, pp. 433–445 (1991).

Swalen et al., "Organic Nonlinear Optical Materials and Their Device Applications for Frequency Doubling, Modulation, and Switching", SPIE, Nonlinear Optical Properties of Organic Materials III, vol. 1337, pp. 2–11 (1990).

Twieg et al., "Nonlinear Optical Epoxy Polymers with Polar Tolan Chromophores", *Mol. Cryst. Liq. Cryst.*, vol. 217, pp. 19–24 (1992).

Jungbauer et al., "Highly Efficient and Stable Nonlinear Optical Polymers via Chemical Crosslinking Under Electric Field", *Appl. Phys. Lett.*, vol. 56, No. 26, pp. 2610–2612 Jun. 25, 1990.

Eich et al., "Novel Second–Order Nonlinear Optical Polymers via Chemical Cross-linking-induced Vitrification Under Electric Field" *J. Appl. Phys.*, vol. 66, #7, pp. 3241–3247, Oct. 1, 1989.

Hubbard et al., "Poled Polymeric Nonlinear Optical Materials. Enhanced Second Harmonic Generation Temporal Stability of Epoxy–Based Matrices Containing a Difunctional Chromophoric Co-Monomer", *Chem. Mater.*, vol. 4, pp. 965–968 (1992).

Hubbard et al., "Poled Polymeric Nonlinear Optical Materials. Enhanced Second Harmonic Generation Stability of Cross-linkable Matrix/Chromophore Ensembles", *Chemistry of Materials*, vol. 1, #2, pp. 167–169, Mar./Apr. 1989.

*Primary Examiner*—Frederick Krass

[57] ABSTRACT

The present invention discloses oriented optical epoxy compositions comprising a reaction product of arylhydrazones with a monomer copolymerizable therewith and to oriented crosslinked polymeric composition comprising the reaction product of an epoxy arylhydrazone or the epoxy composition of the invention with a curing agent. The present invention also discloses processes for making the said compositions.

22 Claims, No Drawings

NONLINEAR OPTICAL EPOXY-CONTAINING COMPOSITIONS AND CROSSLINKED NONLINEAR OPTICAL POLYMERIC COMPOSITION THEREFROM

The present invention relates to epoxy-containing compositions exhibiting nonlinear optical properties on orientation, and to oriented crosslinked polymeric compositions comprising the epoxy-containing compositions.

BACKGROUND OF THE INVENTION

Information may be more rapidly processed and transmitted using optical as opposed to electrical signals. Optical signals can be used to enhance the performance of electronic processors. For example, electronic wires interconnecting integrated circuits (ICs) can be replaced with optical interconnects and the information processed with IC driven electro-optic (EO) modulators. Optical signals in fiber optic communications can be encoded on the optical carrier using EO modulators. In both of these processes, nonlinear optical materials with second-order nonlinear optical activity are necessary to effect modulation of the light signal.

Nonlinear optical materials can also be used for frequency conversion of laser light. Such a conversion is desirable in many applications. For example, optical memory media are presently read using 830 nm light from diode lasers. The 830 nm light wavelength limits the spot sizes which can be read and hence the density of data stored on the optical memory media. In fiber optic communications, light wavelengths of 1.3 μm or 1.5 μm are desirable due to the low transmission losses of glass fiber at those wavelengths. However, those wavelengths are too long for detection by Si based detectors. It is desirable to frequency double the 1.3 μm or 1.5 μm wavelengths to 650 nm or 750 nm wavelengths where Si based detectors could be used.

Nonlinear optical materials which have been used in electro-optic devices have in general been inorganic single crystals such as lithium niobate (LiNbO$_3$) or potassium dihydrogen phosphate (KDP). More recently, nonlinear optical materials based on organic molecules, and in particular polar aromatic organic molecules have been developed.

Organic nonlinear optical materials have a number of potential advantages over inorganic materials. First, organic nonlinear optical materials have higher NLO activity on a molecular basis. Organic crystals of 2-methyl-4-nitroaniline have been shown to have a higher nonlinear optical activity than that of LiNbO$_3$. Second, the nonlinear optical activity of the organic materials is related to the polarization of the electronic states of the organic molecules, offering the potential of very fast switching times in EO devices. The time response of the organic nonlinear optical system to a light field is on the order of 10 to 100 femtoseconds. In contrast, a large fraction of the second order polarizability in the inorganic crystals in EO applications is due to lattice vibrations in the crystal, slowing the time-response of the materials. In addition, the low dielectric constant of the organic materials (e.g., 2-5 Debye at 1MHz) compared to the inorganic materials (e.g., 30 Debye at 1MHz) enables higher EO modulator frequencies to be achieved for a given power consumption. Third, the organic materials can be easily fabricated into integrated device structures when used in polymer form.

One of the promising and recent approaches to making stable nonlinear optically active organic materials involves forming highly crosslinked networks where polar molecules are polymerized directly into the polymer reagent matrix during the poling process. Eich et al., *J. Appl. Phys.*, 66(7), Oct. 1, 1989, pp 3241-3247, discloses the preparation of nonlinear optically active crosslinked polymer networks from the reaction of epoxides, with and without nonlinear optic dye moieties, and NLO active di- and tri-functional amines, in which the NLO amine is attached to the network by two chemical bonds. Jungbauer et al., *Appl. Phys. Lett.*, 56(26), Jun. 25, 1990, pp 2610-2612, discloses a cross-linked polymer network by reacting a diepoxide with a trifunctional amine in which the NLO active group is attached to the crosslinked polymer network by only one chemical bond. European Patent Application No. 0 474 402 A2 discloses multi-functional chromophore containing polymerizable compounds which are capable of being polymerized into a crosslinked network.

Another approach to making nonlinear optically active organic materials involves side chain liquid crystalline polymers, with the NLO chromophore in the side chain as disclosed in U.S. Pat. Nos. 4,855,376, 4,948,532 and 4,933,112.

Still another approach is disclosed in Allen et. al., *J. Appl. Phys.*, 64(5), Sep. 1, 1988, pp 2583-2589, and involves making nonlinear optically active, single crystal structures of highly conjugated molecules based on substituted dihydropyrazoles.

There is a continuing effort to develop new nonlinear optical polymers with increased nonlinear optical susceptibilities and enhanced stability of nonlinear optical effects.

It is an object of this invention to make polymeric compositions incorporating organic molecular structures which exhibit NLO activity upon orientation. It is an additional object of the present invention that the polymers comprising the NLO molecular structures or chromophores have relatively high glass transition temperatures.

It is still a further object of the invention to provide organic polymeric materials with larger and thermally more stable second order nonlinear optical properties than presently used organic electro-optic materials.

SUMMARY OF THE INVENTION

In one aspect, the present invention is an oriented composition comprising the reaction product of:

A) a compound corresponding to the Formula:

wherein Ar is an aromatic hydrocarbyl or heterocylic radical, substituted with at least one electron withdrawing group, and containing up to 30 non-hydrogen atoms, and optionally substituted with an OR' group; A is independently at each occurrence either R or a C$_{6-30}$ aromatic hydrocarbyl or heterocylic radical optionally substituted with an OR' group; R' is a hydrogen, epoxy or an alkylepoxy group; and R is a hydrogen or a C$_1$-C$_{20}$ hydrocarbyl radical; provided there are at least two aromatically substituted OR' groups groups in the compound; and B) a monomer copolymerizable therewith.

In another aspect, the present invention is an oriented polymeric composition comprising a reaction product of the compound of Formula (I) wherein R' is an epoxy or an alkylepoxy group, with a curing agent.

In yet still another aspect, the present invention is an oriented crosslinked polymeric composition comprising a reaction product of the above epoxy composition with a curing agent.

In yet still another embodiment, the present invention relates to a process for preparing an oriented crosslinked polymeric composition, comprising substantially simultaneously applying an external field and thermally annealing the reaction product of an epoxy composition with a curing agent, the epoxy composition comprising recurring moieties derived from a compound corresponding to the Formula I. The application of the external field and thermal annealing are carried out for a period of time sufficient to form a crosslinked composition having nonlinear optical properties.

In yet still another embodiment, the present invention is a process for preparing an oriented crosslinked polymeric composition comprising simultaneously polymerizing and applying an external field to a reaction mixture of the compound Formula (I) wherein R' is an epoxy or an alkylepoxy group of a curing agent.

In yet still another embodiment, the present invention is a device comprising the nonlinear optical epoxy-containing composition of the invention or the oriented polymeric composition of the invention.

DETAILED DESCRIPTION OF THE INVENTION

The term "orientation" as used herein refers to the alignment of molecular dipoles upon the application of an external field to a molecule or moieties derived therefrom according to the methods described herein, or by some other means, such that the molecule, or the moieties derived therefrom exhibit nonlinear optical activity.

The phrase "oriented polymeric composition" refers to the polymeric composition following orientation as described above.

The term "external field" as used herein refers to an electric, magnetic or mechanical stress field which is applied to a substrate of mobile organic molecules to induce dipolar alignment of the molecules parallel to the field.

The phrase "aromatically substituted" herein refers to substituents that are directly attached to a hydrocarbyl or heterocyclic aromatic ring represented by radicals Ar and A.

The term "electron donating" as used herein refers to organic substituents which contribute n-electrons to a conjugated electronic structure.

The term "conjugated" group, as employed herein refers to a moiety containing alternating double or triple bonds which has the ability to transfer electronic charge. Conjugated moieties generally include groups which have, for example, a hydrocarbyl diradical comprising a single aromatic ring, multiple fused rings or multiple aromatic rings linked by carbon-carbon, carbon-nitrogen, or nitrogen-nitrogen double bonds. The conjugated groups may be substituted with pendant radicals such as alkyl, aryl, cyano, halo and nitro groups.

The term "electron withdrawing", as employed herein, refers to any substituent which attracts the electrons from a conjugated electron structure, thereby providing a polarized resonating structure. A quantification of the level of electron-withdrawing capability is given by the Hammett $\sigma$ (sigma) constant. This well known constant is described in many references, for instance, J. March, *Advanced Organic Chemistry*, (McGraw Hill Book Company, N.Y., 1977 edition) pp. 251–259. The Hammett constant values are negative for electron donating groups ($\sigma_p = -0.66$ for $NH_2$) and positive for electron withdrawing groups ($\sigma_p = 0.78$ for a nitro group, $\sigma_p$ indicating para substitution.)

Preferred electron withdrawing groups are those having a Hammett constant of ($\sigma_p$) at least 0.50, and more preferably at least 0.60.

Illustrative of the electron withdrawing groups useful in the present invention include: $-NO_2$, $-SO_2R''$, $-SO_2CH_2F$, $-SO_2CHF_2$, $-SO_2CF_3$, $-S(-NSO_2CF_3)CF_3$, $-CF_3$, $-CO_2R''$, $-COCF_3$, cyano, cyanovinyl, dicyanovinyl, and tricyanovinyl, wherein $R''$ is hydrogen or a $C_1$ to $C_{20}$ hydrocarbyl radical.

Epoxy compositions

The epoxy compositions of the invention comprise recurring moieties derived from the arylhydrazone of Formula (I), which exhibit nonlinear optical properties upon orientation. The arylhydrazones are described in U.S. Pat. No. 5,208,299, the entire contents of which are incorporated herein by reference.

Illustrative of Ar radicals in the arylhydrazone of Formula (I) include:

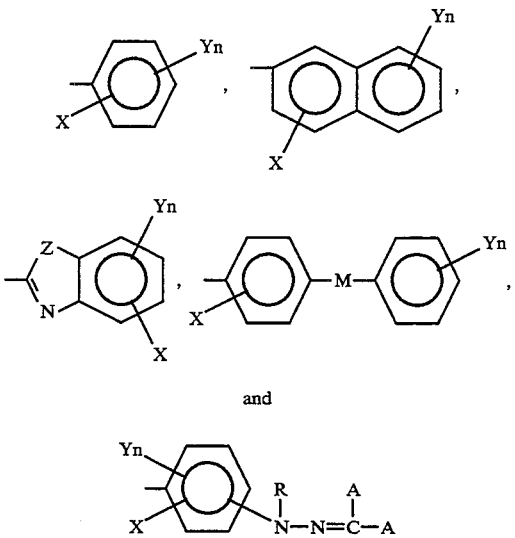

wherein X is either hydrogen or OR'; Z is selected from a group consisting of O, S and NR; M is either a covalent bond or a divalent conjugated group; Y is an electron-withdrawing group; n is an integer from 1 to 4; and R and R' are as defined hereinabove.

Illustrative of A radicals in the arylhydrazone of Formula (I) include:

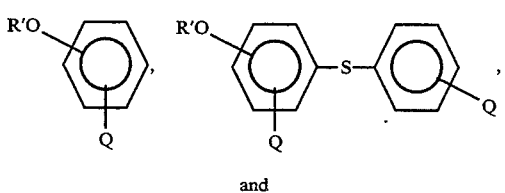

and

-continued

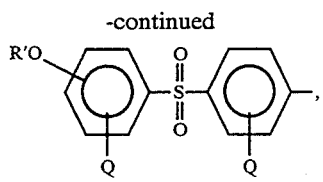

wherein Q is selected from a group consisting of hydrogen, OR', R, RO, RS, $R_2N$,

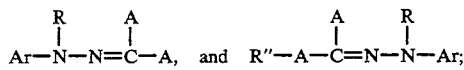

where A, R, R', and Ar are as previously defined, and R" is a divalent substituted or unsubstituted hydrocarbyl group containing 1 to 20 carbon atoms.

The arylhydrazones can be suitably prepared by the reaction of a suitable hydrazine with a compound containing one or more carbonyl groups, especially aldehyde or ketone.

Illustrative but not limiting examples of the hydrazines include 4-nitrophenylhydrazine, 2,4-dinitrophenylhydrazine, N'-methyl-N'-3-(hydroxy-4-nitrophenyl) hydrazine, N'-methyl-N'-4-(nitrophenylhydrazine), 6-nitro-2-benzothioazolylhydrazine, N'-methyl-N'[4-(p-hydroxyphenylsulfonyl)phenyl]hydrazine, 2,4-dinitro-1,5-bis(N'-hydrazino)benzene, 2,4-bis(methylsulfonyl)phenylhydrazine, 4-(methylsulfonyl)phenylhydrazine, and 4-(tricyanovinyl)phenylhydrazine. Preferred hydrazines useful for the present invention are substituted nitrophenylhydrazines.

Suitable carbonyl groups containing reactants for the purpose of this invention are of the general formula:

where A is independently at each occurrence as previously defined.

Illustrative but not limiting examples of such compounds are 4,4'-dihydroxybenzophenone, 4,4'-bis-(4-hydroxyphenylthio)benzophenone, 4-hydroxybenzaldehyde, 3-hydroxy-4-methoxybenzaldehyde, 5,5'-methylene-bis-salicylaldehyde, 1,3-diacetylbenzene, 4,4'-bis(4-hydroxyphenylsulfonyl)benzophenone and 2,4-dihydroxybenzaldehyde.

The methods of preparing the arylhydrazones are described in U.S. Pat. No. 5,208,299 which has been incorporated herein by reference. The reaction of the above-described carbonyl compounds with the above-described hydrazines provides hydroxy arylhydrazones.

The hydroxy arylhydrazones obtained from the above-described carbonyl compounds and the arylhydrazines are reacted with an excess of epoxide such as epihalohydrin, followed by dehydrohalogenation to obtain the epoxy arylhydrazones containing at least two epoxy or alkylepoxy groups. The alkyl group in the alkylepoxy is represented by a $C_1$-$C_{20}$ hydrocarbyl group.

The epoxy arylhydrazone can be reacted with a difunctional monomer, using the well known procedure of epoxy resin chain extension. See for example, U.S. Pat. No. 4,438,254, and references contained therein. Alteration of the mole ratios of the difunctional monomer and the epoxy can provide products of varying molecular weight and varying end-group functionality, as can be predicted from the established kinetics of step-growth polymerization. The epoxy compositions of the invention are preferably prepared using a molar excess of the epoxy arylhydrazone to provide a composition that is statistically likely to contain epoxy end groups. Other epoxides listed hereinbelow may be advantageously added to the reaction mixture.

The mole ratio of the epoxy to difunctional monomer is in the range of 2:1 to about 1:1, such that at least about 10 mole percent of the mixture is derived from the epoxy arylhydrazone of Formula (I).

The hydroxy arylhydrazones can also be reacted with a difunctional monomer, for example, diepoxides listed below, including the above-described epoxy arylhydrazones to obtain the epoxy compositions of the invention. Thus, the arylhydrazone represented by Formula (I) containing at least two aromatically substituted OR' groups can be suitably polymerized to obtain the epoxy compositions of the invention according to methods well known to those skilled in the art of epoxy resins. See, for example, *Encyclopedia of Polymer Science and Technology*, 2nd Edition, pp. 323–331.

Suitable difunctional monomers for copolymerizing with the arylhydrazone of Formula (I) include diepoxides, diphenols, dithiols, diacids and difunctional amines.

Diphenols which can be employed in the practice of the present invention include the bisphenols described in U.S. Pat. Nos. 5,115,075; 4,480,082 and 4,438,25 4, and in copending U.S. applications Ser. No. 800, 340, filed on Nov. 26, 1991, now abandoned, and Ser. No. 884, 673, filed on May 18, 1992, now U.S. Pat. No. 5,246,751, all of which are incorporated herein by reference. Preferred diphenols include 4,4'-isopropylidenebisphenol (bisphenol A), 4,4'-sulfonyldiphenol, 4,4'-oxydiphenol, 4,4'-methylenediphenol, 4,4'-thiodiphenol, 9,9-bis(4-hydroxyphenyl)fluorene, 4,4'-biphenol, 4,4'-dihydroxybenzophenone, hydroquinone, resorcinol, and 3,3', 5,5'-tetrabromobisphenol A. More preferred phenols are 4,4'-isopropylidenebisphenol (bisphenol A), 9,9-bis(4-hydroxyphenyl)fluorene, hydroquinone, resorcinol, 4,4'-sulfonyldiphenol, 4,4'-thiodiphenol, 4,4'-oxydiphenol, and 4,4'-biphenol. Most preferred phenols are 4,4'-isopropylidenebisphenol (bisphenol A), 4,4'-sulfonyldiphenol, 4,4'-oxydiphenol, and 9,9-bis(4-hydroxy-phenyl)fluorene. The diphenols may include the hydroxy arylhydrazone of the invention.

Dithiols which can be employed in the practice of the present invention include those represented by the formula HS-R'''—SH, wherein R''' is a hydrocarbylene or a divalent aromatic moiety. Preferably, R''' is (1) alkylene or cycloalkylene which optionally contains a heteroatomic moiety such as oxygen, sulfur, sulfonyl, or sulfoxyl or (2) arylene which optionally contains a heteroatomic moiety and optionally substituted with alkyl, alkoxy, halo , nitro, cyano or cycloalkyl groups. More preferred dithiols include 1,4-butanedithiol, 1,5-pentanedithiol, mercaptoethyl ether, 1,6-hexanedithiol, and 4,4'-dimercaptodiphenyl ether (DMPE). The most preferred dithiol is DMPE. Dithiols and processes for preparing them are well known. See, for example, U.S. Pat. No. 3,326,981 and Sutter Scrutchfield, *Journal of the American Chemical Society*, Vol. 58, p. 54, 1936.

Dicarboxylic acids which can be employed in the practice of the present invention include 4,4'-biphenyldicarboxylic acid, 2,6-naphthalenedicarboxylic acid, isophthalic acid and terephtalic acid. Preferred diacids include isophthalic acid and terephthalic acid. Most preferred diacid is terephthalic acid.

Difunctional amines which can be employed in the practice of the present invention include amines having two reactive hydrogen atoms such as ethanolamine, propanolamine, 2-aminopropionamide, aniline, 4-hydroxyaniline, anisidine, benzylamine, piperazine and 2,5-dimethylpiperazine.

Diepoxides which can be employed in the practice of the present invention include the 9,9-bis(4-hydroxyphenyl)fluorene, hydroquinone, resorcinol, 4,4'-sulfonyldiphenol, 4,4'-thiodiphenol, 4,4'-oxydiphenol, 4,4'-dihydroxybenzophenone, tetrabromoisopropylidenebisphenol, 4,4'-biphenol, 4,4'-dihydroxybiphenylene oxide, bis(4-hydroxyphenyl)methane, α,α-bis(4-hydroxyphenyl)ethylbenzene, 2,6-dihydroxynaphthalene and 4,4'-isopropylidene bisphenol (bisphenol A). More preferred diglycidyl ethers are the diglycidyl ethers of 9,9-bis(4-hydroxyphenyl)fluorene, hydroquinone, resorcinol, 4,4'-sulfonyldiphenol, 4,4'-thiodiphenol, 4,4'-oxydiphenol, 4,4'-dihydroxybenzophenone, tetrabromoisopropylidenebisphenol, 4,4'-biphenol, 4,4'-dihydroxybiphenylene oxide, bis(4-hydroxyphenyl)methane, α,α-bis(4-hydroxyphenyl)ethyl-benzene, 2,6-dihydroxynaphthalene and 4,4'-isopropylidene bisphenol (bisphenol A). Most preferred diglycidyl ethers are the diglycidyl ethers of 4,4'-isopropylidene bisphenol (bisphenol A), 4,4'-sulfonyldiphenol, 4,4'-oxydiphenol, 4,4'-dihydroxybenzophenone, and 9,9-bis(4-hydroxyphenyl)fluorene. Diepoxides also include the diglycidyl ethers of arylhydrazones described above.

The incorporation of the NLO active moieties derived from the arylhydrazones has a number of advantages. High levels of NLO chromophore functionalization can be achieved without increasing the scattering losses of waveguides fabricated from the polymer. The addition of the groups which add to the NLO activity of the polymer do not plasticize the polymer and lower the polymer $T_g$. In fact, such modifications can raise the polymer $T_g$. Furthermore, the fact that the NLO chromophore is inherent to the polymer backbone increases the orientational stability of the NLO chromophores, reducing the temporal decay of the NLO activity with time. Thus, compositions containing this monomer have the advantage of high $T_g$ and increased orientational stability when fabricated into a nonlinear optical film or other NLO article in comparison to other NLO polymers.

Crosslinked Polymer Compositions

The crosslinked polymeric compositions can be obtained by curing the epoxy arylhydrazone of Formula (I) containing at least two epoxy or alkylepoxy groups or the above-described epoxy compositions with at least one curing agent by methods well known in the art. The polymeric compositions are then oriented as described below to obtain the oriented polymeric compositions of the invention.

Generally, the amounts of the epoxy composition or the epoxy arylhydrazone and the curing agent employed herein are sufficient to provide a cured product. Usually the amounts of the epoxy composition or the epoxy arylhydrazone and the curing agent which provide a ratio of equivalents of curing agent per epoxy group from about 0.5 to about 1.2; preferably from about 0.95 to about 1.05 are used herein.

The curing agents which can be employed herein include, for example, amines, acids or anhydrides thereof, biguanides, imidazoles, urea-aldehyde resins, melamine-aldehyde resins, phenolics, halogenated phenolics, sulfides and combinations thereof. These and other curing agents are disclosed in Lee and Neville's *Handbook of Epoxy Resins*, McGraw-Hill Book Co., 1967. The curing agent may be a compound which exhibits a NLO response. Nonlinear optical active amine curing agents, and crosslinked epoxy polymers thereof, exhibiting nonlinear optical activity are described in now allowed U.S. application Ser. No. 844,340, filed Mar. 3, 1992 and now U.S. Pat. No. 5,279,870, U.S. Pat. No. 5,173,546, issued Dec. 22, 1992, and U.S. Pat. No. 5,112,934, issued May 12, 1992. Suitable curing agents, for example, include 4,4'-diaminodiphenyl sulfone, p-nitroaniline, nitrobenzyl amine, Disperse Orange, methyl nitroaniline, amino nitropyrimidine, 2-6-diamine 4-nitrotoluene, 5-nitrobenzotriazole and combinations thereof, bisphenol A, tetrabromobisphenol A, phenolformaldehyde novolac resins, halogenated phenolformaldehyde resins, hydrocarbonphenol resins and combinations thereof.

It may be advantageous to include commercially available epoxy resins to the polymerization mixture. Some commercial epoxy resins useful in the present invention include, for example, D.E.R. TM 331, D.E.R. TM 332, D.E.R. TM 383, D.E.R. TM 431, D.E.R. TM 736, D.E.R. TM 661, and Tactix TM 742, all commercially available from The Dow Chemical Company.

The thermoset polymeric compositions of the present invention are preferably prepared by making a prepolymer by melt or solution polymerization methods known in the art. The prepolymer is used to form a film by methods described hereinbelow. The film so obtained is cured to provide the crosslinked thermoset polymeric composition of the present invention.

The oriented polymeric composition can be prepared by applying an external field to the polymeric compositions described above. The polymeric compositions of the present invention can be in the form of sheets, films, fibers or other shaped articles formed by conventional techniques. Generally, films are used in testing, electro-optic devices and waveguide applications.

Methods of fabricating films of NLO polymers and the methods of characterization of NLO activity are well known to those skilled in the art. Polymer films are typically fabricated by spin-coating or dip-coating a polymer solution onto a substrate. The substrate used depends on the poling method and method of characterization. For corona poling, a glass substrate such as a microscope slide is typically used. For parallel plate poling, a substrate with an electrically conductive surface is necessary, such as indium-tin-oxide (ITO) coated glass. The coated glass slides can be used directly for corona poling. The coated ITO slides for parallel plate poling require an electrically conductive overlayer, such as sputter-coated gold.

The fabricated NLO film must have a non-centrosymmetric alignment of the dipolar segments throughout the bulk of the polymer film. This is achieved by poling the filmy or applying an electric field across the film. In corona poling, the field results form a discharge between a wirer such as tungsten, suspended above the film and a grounded heater block. The corona poling technique is described further by M. A. Mortazavi et al., *J. Opt. Sc. Am.*, B 6 (1989). In parallel plate poling a voltage is applied across the two electrode layers. In both procedures a voltage is applied at elevated temperatures, near the polymer $T_g$ (approximately 5° to 10° C. above the onset of $T_g$ as measured by DSC). The field is left on for at least a few minutes and the sample cooled with the field on to maintain the orientation of the dipolar segments.

The oriented polymeric compositions of the invention can be prepared by substantially simultaneously applying an external field and thermally annealing the reaction product of the epoxy-containing composition comprising recurring moieties derived from the arylhydrazone of Formula I with a curing agent for a period of time sufficient to form a material having nonlinear optical properties. This process for producing a nonlinear optical polymeric film comprises poling the film to orient the NLO moieties by the methods described above, lowering the temperature to 10° to 50° C. below the glass transition temperature, and annealing for a period of time whereby a stable NLO polymeric film is obtained. This "annealing" step is carried out so as to cause a reduced free volume in the film and thus less room for NLO moieties to randomly reorient themselves which lead to a decrease in the NLO signal. Thus this annealing process during the polymer orientation may advantageously improve the stability of the polymer. A specific example illustrating the advantages of thermally annealing and poling the polymeric film is set forth below.

Another method of orientation of the thermoset polymer of the present invention for producing nonlinear optical materials includes polymerizing the prepolymer of a thermoset polymeric composition of the invention while the prepolymer is under an electric field such that the nonlinear optical moieties are aligned in the electric field before complete polymerization of the prepolymer takes place. This method of orientation will produce less stress on the ultimate polymer network than if the electric field is applied after the NLO moieties are incorporated into the backbone of the polymer.

The oriented film fabricated from the polymers of this invention can be characterized for their NLO activity by a Maker Fringe Rotation Second Harmonic Generation Technique which is well known to those skilled in the art. See for example, Singer et al., *Appl. Phys. Lett.*, 49, ( 1986 ) 2448-250.

The oriented polymeric film is used as a nonlinear optical medium in Mach-Zehnder intensity modulators, directional couplers, switches, frequency stabilizers, optical parametric devices, phase modulators, and passive waveguiding devices, as described in T. A. Tumolillo, Jr. "Multilevel registered polymeric Mach-Zehnder Intensity modulator array", *Applied Physics Letters*, 62(24), 14 Jun. 1993, U.S. Pat. No. 5,119,228, and G. R. Mohlmann et al., *Nonlinear Optical Properties of Organic Materials III*, SPIE Vol. 1337, (1990), the relevant portions of which are incorporated herein by reference.

The following preferred specific embodiments are to be construed as merely illustrative, and not limitative of the remainder of the disclosure in any way whatsoever. In the following examples, all temperatures are set forth uncorrected in degree Celsius; unless otherwise indicated, all parts and percentages are by weight.

EXAMPLE 1

Diglycidyl Ether of Bis(N'-methyl-4-nitrophenylhydrazone) of 5,5'-methylene-bis-salicylaldehyde (I)

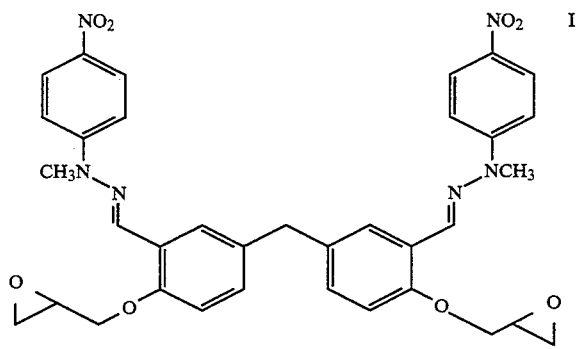

Compound I was prepared using bis(N'-methyl-4-nitrophenylhydrazone) of 5,5'-methylene-bis-salicylaldehyde (BHBF) as the precursor diphenol.

BHBF was prepared in accordance with the procedure described in Example 7 of U.S. Pat. No. 5,208,299. A mixture of BHBF, epichlorohydrin (90 mL), and benzyltrimethylammonium chloride (0.15 g, 0.8 mmol) was stirred at 85° C. for 16 hours. The mixture was cooled to 0° C. (ice/water bath) and sodium hydroxide (2 mL of a 50 percent aqueous solution) was added. The mixture was allowed to warm to room temperature and was stirred overnight. The mixture was diluted with dichloromethane and was washed with water. The organic layer was removed and dried over anhydrous magnesium sulfate, which was removed by filtration. Removal of solvents gave the product as a red solid. The product was purified by recrystallization from a hot chloroform/methanol mixture. The product was dried in a vacuum oven. $^1$H NMR (d6-DMSO) d 7.79 (dd, J1=171.0 Hz, J2=9.5 Hz, 4H), 7.83 (m, 1H), 7.24 (d, J=8.5 Hz, 1H), 7.07 (d, J=8.6 Hz, 1H), 4.42 (d, J=11.5 Hz, 1H), 3-99 (m, 2H), 3.51 (s, 3H), 3.41 (m, 1H), 2.87 (m, 1H), 2.77 (m, 1H). 13C NMR (d6-DMSO) 156.03, 153.12, 140.23, 135.40, 133.74, 131.86, 126.81, 126.50, 124.81, 114.90, 114.57, 71.02, 50.97, 44.93, 33.48.

EXAMPLE 2

Epoxy Composition from D.E.R. ™ 332 and BHBF(II)

A 100 mL minireactor, equipped with mechanical stirrer, condenser, and $N_2$ inlet, was charged with D.E.R. ™ 332 epoxy resin (5.543 g, 16.2 mmol, 2 equivalent s/diphenol, 171.22 g/equiv e.e.w., washed), BHBF (4.489 g, 8.09 mmol,), and ethyltriphenyl-phosphonium iodide (0.34 g, 0.81 mmol, 10 mol percent). DOWANOL ® PM glycol ether (25 mL) was added under $N_2$ and the mixture was heated to reflux for 24 hours. The mixture was allowed to cool and DMF (20 mL) was added to dissolve the orange slurry. The product was isolated by pouring the solution into water and collecting the product by suction filtration. The product was allowed to air dry, and was then vacuum dried for 5 hours. Vacuum drying was started at 75° C. but the product began to fuse and drying was continued at room temperature. Obtained 8.40 g product (84 percent yield). $^1$H NMR (d6-DMSO)δ8.10, m; 7.82, s, br; 7.47, m; 7.20, m; 7.05, m; 6.83, m; 5.44, s; 4.3–4.0, m; 3.80, m;

3.42, m; 2.83, t; 2.70, m; 1.58, s; 1.50, s. 13C NMR (d6-DSMO) 156.18, 155.91, 155.87, 155.07, 151.81, 151.79, 142.58, 138.90, 133.81, 133.04, 132.97, 130.56, 127.31, 127.25, 125.38, 125.15, 123.58, 119.46, 113.82, 113.78, 113.35, 113.17, 70.30, 69.06, 68.75, 67.38, 49.63, 43.66, 41.04, 32.19, 32.14, 30.58.

EXAMPLE 3

Epoxy Composition from I and 9,9-bis(4-hydroxyphenyl)fluorene (BHPF) (3:2) (III)

This epoxy composition was prepared in the manner described above for Example 2, using 3 parts of compound I and 2 part (BHPF). The $^1$H and 13C NMR spectra of the product were consistent with the expected structure.

EXAMPLE 4

Epoxy Composition From Bisphenol A Diglycidyl Ether and 4-nitro-phenylhydrazone of bisphenol K (NPHBK) (IV)

This epoxy composition was prepared in the manner described above for Example 2, using 2 parts bisphenol A diglycidyl ether and one part NPHBK. NPHBK was prepared as described in Example 1 of U.S. Pat. No. 5,208,299. The $^1$H and 13C NMR spectra of the product were consistent with the expected structure.

Preparation of Films for NLO Activity Measurement

Thin films (about 1–5 μm) were prepared by spin coating from either a prepolymer or epoxy composition using a Solitec Model 5100 spin coater. Typically, the solids content of the solution was about 30–33 weight percent. Solvents used are listed below for each example. Substrates were ITO coated borosilicate glass from Donnelly Applied Films Corporation.

The cast films were air dried for at least 24 hours, followed by drying at elevated temperatures in a nitrogen atmosphere and under vacuum, and film thicknesses were measured on a Tencor Instruments Alpha Step 200 profilimeter. Films were then coated with 140–250 Å gold for parallel plate poling experiments. The d33 values were determined by second harmonic generation (SHG) measurements using the Maker Fringe rotation method, (see K. D. Singer et al., *Appl. Phys. Lett.*, 49, 248 (1986)). A fundamental wavelength of 1579 nm was used. A y-cut quartz crystal was used as a reference.

Oriented Crosslinked Polymeric Compositions

Examples 5A–8 describe the preparation of the oriented crosslinked polymeric compositions of the invention.

EXAMPLE 5A

A solution containing compound II (2.0 g, 0.0032 epoxide eq) and 4,4'-diaminodiphenyl sulfone (DADS) (0.20 g, 0.0032 amine eq) was prepared in 5 ml dimethylacetamide (DMAc). This solution was used directly to prepare films by spin coating at 1500 rpm for 40 sec and allowing the films to air dry for about 24 hours. The films were then dried in a nitrogen purged oven for 1 hour at 100° C. and 1 hour at 150° C., and further dried for 1 hour at 150° C. under vacuum. The films were then simultaneously poled and cured at 150° C. for 1 hour with an applied field of 50V/μm.

EXAMPLE 5B

Another set of films was prepared by spin coating with the above-obtained solution. The films were dried at 100° C. for 1 hour, 150° C. for 1 hour, and 180° C. for 1 hour. The films were then poled at 150° C. for 10 minutes with an applied field of 50 V/μm. The resulting films were about 2.0 μm thick.

EXAMPLE 6

A solution containing compound II, (1.97 g, 0.0032 epoxide eq), methyltetrahydrophthalic anhydride (MTHPA) (0.54 g, 0.0033 anhydride eq) and benzyldimethyl amine catalyst were prepared (BDMA, 0.014 g) in 5 ml DMAc. The solution had limited stability at room temperature once the BDMA was added and was therefore used immediately to spin coat films at 1,000 rpm for 40 seconds, which were allowed to air dry for about 24 hours. The films were then dried in a nitrogen purged oven for 1 hour at 100° C. and 1 hour at 150° C. The films were then dried for 1 hour at 150° C. in a vacuum oven and then 1 hour at 180° C. in the nitrogen purged oven. The resulting films were 2.1 μm thick.

Then films were poled for 10 minutes at 150° C. with an applied field of 50 V/μm.

EXAMPLE 7

Compound III (3.5 g, 0.0021 epoxide eq), D.E.R. ™ 332 epoxy resin (0.38 g), commercially available from The Dow Chemical Company, and DADS (0.13 g, 0.0021 amine eq) were dissolved in 9 ml DMAc. The solution was used to spin coat films at 1,000 rpm for 40 seconds, which were allowed to air dry for about 24 hours. The films were then dried in a nitrogen purged oven for 1 hour at 100° C. and 1 hour at 150° C. The films were then dried for 1 hour at 150° C. in a vacuum oven and then 1 hour at 180° C. in a nitrogen purged oven. The resulting films were about 5.0–5.2 μm thick.

The films were then poled for 10 minutes at 190° C. with an applied field of 50 V/μm.

EXAMPLE 8

Preparation of DADS/Compound I/Tactix ™ 742 Prepolymer

Compound I (2.02 g, 0.0058 epoxide eq), Tactix ™ 742 (1.33 g, 0.0083 epoxide eq), commercially available from The Dow Chemical Company, DADS (0.89 g, 0.014 amine hydrogen eq), and 10 ml DMAc were added to a 100 mL 3-neck round bottom flask and purged on a Schlenk line for about 30 minutes with argon. All solids did not dissolve at room temperature. Heating was commenced and by 90° C. all solids had dissolved. The solution was refluxed for 5 hours at 160° C.

Films were spin coated from the above solution at 1,000 rpm for 30 seconds. After air drying overnight, they were dried in a N$_2$ purged clean room oven for 1 hour at 100° C., then 1 hour at 150° C. in a vacuum oven. The resulting film thicknesses were about 1.8 μm.

The films were simultaneously poled and cured in a nitrogen-purged oven for 1.5 hours at 180° C., 1 hour at 200° C., and 1 hour at 216° C. The poling field of 50 V/μm was applied after 35 minutes at 180° C.

The d$_{33}$ values for Examples 5A–8 were determined using a fundamental wavelength of 1579 nm, as described above. The values obtained are set forth in Table I below.

TABLE I

| Example | $d_{33}$ ($10^{-9}$ esu) | Parallel Plate Poling |
|---|---|---|
| 5A | 9 | during cure |
| 5B | 9 | after cure |
| 6 | 6 | after cure |
| 7 | 10 | after cure |
| 8 | 6 | after cure |

Stability of Thermoset Polymers

The thermal stability of three polymers was evaluated by monitoring the SHG signal as the temperature was increased at a rate of 5° C./minute from room temperature to 150° C. and 180° C., for Example 5A, 7 and 8, respectively. The results are set forth in Table II below.

TABLE II

| Temperature (°C.) | Depoling Data for Thermoset Polymers | | |
|---|---|---|---|
| | Relative SHG Signal | | |
| | Example 5A | Example 7 | Example 8 |
| 22 | 1.00 | 1.00 | 1.00 |
| 80 | 1.00 | 1.00 | 0.97 |
| 100 | 1.00 | 0.96 | 0.94 |
| 140 | 0.80 | 0.85 | 0.95 |
| 150 | 0.56 | 0.82 | 0.79 |
| 170 | — | 0.60 | 0.66 |
| 175 | — | 0.54 | 0.63 |
| 180 | — | 0.38 | 0.58 |

What is claimed is:

1. A crosslinked oriented polymeric composition comprising a reaction product of a compound of Formula (I)

wherein Ar is an aromatic hydrocarbyl or heterocylic radical containing up to 30 non-hydrogen atoms, substituted with at least one electron withdrawing group, and optionally substituted with an OR' group; A is independently at each occurrence either R or a $C_{6-30}$ aromatic hydrocarbyl or heterocylic radical optionally substituted with an OR' group, wherein R' is an epoxy or an alkylepoxy group, and R is a hydrogen or a $C_1$-$C_{20}$ hydrocarbyl radical; provided there are at least two aromatic OR' groups in the compound; with a curing agent.

2. A crosslinked oriented polymeric composition comprising a reaction product of an epoxy composition comprising a reaction product of:
A) a compound corresponding to the Formula:

wherein Ar is an aromatic hydrocarbyl or heterocylic radical containing up to 30 non-hydrogen atoms, substituted with at least one electron withdrawing group, and optionally substituted with an OR' group; A is independently at each occurrence either R or a $C_{6-30}$ aromatic hydrocarbyl or heterocylic radical optionally substituted with an OR' group, wherein R' is hydrogen, epoxy, or alkylepoxy; and R is a hydrogen or a $C_1$-$C_{20}$ hydrocarbyl radical; provided there are at least two aromatic OR' groups in the compound; and B) a monomer condensation copolymerizable therewith, said epoxy composition containing epoxy end groups with a curing agent.

3. The composition of claim 1 or 2, wherein Ar is selected from the group consisting of:

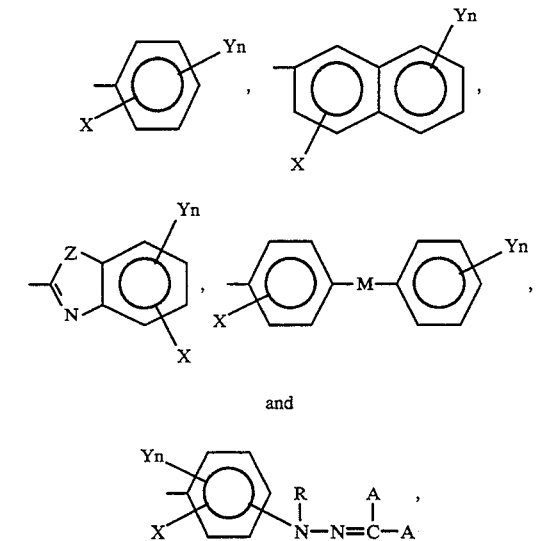

wherein X is either hydrogen or OR'; Z is selected from the group consisting of O, S and NR; M is either a covalent bond or a divalent conjugated group; Y is an electron-withdrawing group; n is an integer from 1 to 4; and R' and R areas defined hereinabove.

4. The composition of claim 3 wherein the divalent conjugated group is selected from the group consisting of —C≡C—, —CR=CR—, —CR=CR—CR=—, —CR=N—, —N=CR—, and —N=N—, wherein R is as defined hereinabove.

5. The composition of claim 3 wherein Y is selected from the group consisting of $NO_2$, $SO_2R$, $SO_2CH_2F$, $SO_2CHF_2$, $SO_2CF_3$, $S(NSO_2CF_3)CF_3$, $CF_3$, $CO_2R$, $COCF_3$, cyano, cyanovinyl, dicyanovinyl, and tricyanovinyl, wherein R is a hydrogen or a $C_1$ to $C_{20}$ hydrocarbyl group.

6. The composition of claim 1 or 2, wherein A at each occurrence is independently selected from the group consisting of:

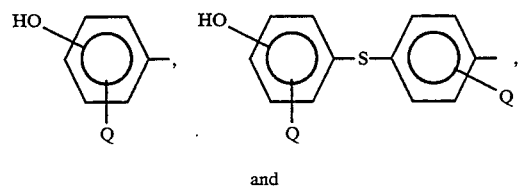

wherein Q is selected from the group consisting of hydrogen, OR', R, RO, RS, $R_2N$,

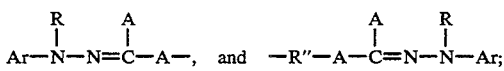

where A, R', R and Ar are as previously defined and R" is a divalent substituted or unsubstituted hydrocarbyl group containing from 1 to 20 carbon atoms.

7. The composition of claim 1 or 2, wherein the compound of Formula (I) is 4-nitrophenylhydrazone of bisphenol K.

8. The composition of claim 1 or 2, wherein the compound of Formula (I) is diglycidyl ether of Bis(N'-methyl-4-nitrophenylhydrazone) of 5,5'-methylene-bis-salicylaldehyde.

9. The composition of claim 1 or 2 wherein the curing agent is selected from the group consisting of 4,4'-diaminodiphenyl sulfone, p-nitroaniline, nitrobenzyl amine, 4-(4-nitrophenylazo)aniline, methyl nitroaniline, amino nitropyrimidine, 2-6-diamine 4-nitrotoluene, 5-nitrobenzotriazole and combinations thereof, bisphenol A, tetrabromobisphenol A, phenolformaldehyde novolac resins, halogenated phenolformaldehyde resins, hydrocarbonphenol resins and combinations thereof.

10. A process for preparing a crosslinked oriented polymeric composition, comprising substantially simultaneously applying an external field and thermal annealing the reaction product of an epoxy composition comprising a reaction product of:

A) a compound corresponding to the Formula:

 (I)

wherein Ar is an aromatic hydrocarbyl or heterocylic radical containing up to 30 non-hydrogen atoms, substituted with at least one electron withdrawing group, and optionally substituted with an OR' group; A is independently at each occurrence either R or a $C_{6+}$ aromatic hydrocarbyl or heterocylic radical optionally substituted with an OR' group, wherein R' is hydrogen, epoxy, or alkylepoxy; and R is a hydrogen or a $C_1$-$C_{20}$ hydrocarbyl radical; provided there are at least two aromatic OR' groups in the compound; and B) a monomer condensation copolymerizable therewith, said epoxy composition containing epoxy end groups and a curing agent for a period of time sufficient to form a composition having nonlinear optical properties.

11. A process for preparing a crosslinked oriented polymeric composition, comprising substantially simultaneously applying an external field and thermally annealing the reaction product of the compound of Formula (I)

 (I)

wherein Ar is an aromatic hydrocarbyl or heterocylic radical containing up to 30 non-hydrogen atoms, substituted with at least one electron withdrawing group, and optionally substituted with an OR' group; A is independently at each occurrence either R or a $C_{6-30}$ aromatic hydrocarbyl or heterocylic radical optionally substituted with an OR' group, wherein R' is an epoxy or an alkylepoxy group; and R is a hydrogen or a $C_1$-$C_{20}$ hydrocarbyl radical; provided there are at least two aromatic OR' groups in the compound; and a curing agent for a period of time sufficient to form a composition having nonlinear optical properties.

12. A process of preparing a crosslinked oriented polymeric composition, comprising substantially simultaneously polymerizing and applying an external field to the reaction product of the compound of Formula (I)

 (I)

wherein Ar is an aromatic hydrocarbyl or heterocylic radical containing up to 30 non-hydrogen atoms, substituted with at least one electron withdrawing group, and optionally substituted with an OR' group; A is independently at each occurrence either R or a $C_{6-30}$ aromatic hydrocarbyl or heterocylic radical optionally substituted with an OR' group, wherein R' is an epoxy or an alkylepoxy group; and R is a hydrogen or a $C_1$-$C_{20}$ hydrocarbyl radical; provided there are at least two aromatic OR' groups in the compound; and a curing agent for a period of time sufficient to form a composition having nonlinear optical properties.

13. The process of claim 10, 11 or 12 wherein Ar is selected from the group consisting of:

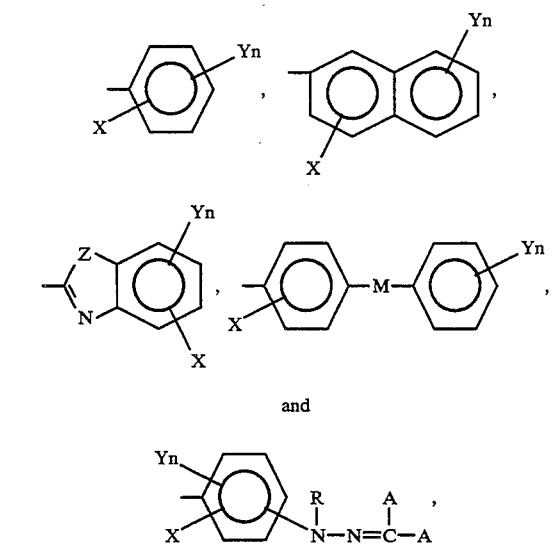

wherein X is either hydrogen or OR'; Z is selected from the group consisting of O, S and NR; M is either a covalent bond or a divalent conjugated group; Y is an electron-withdrawing group; n is an integer from 1 to 4; and R' and R are as defined hereinabove.

14. The process of claim 13, wherein the divalent conjugated group is selected from the group consisting of —C≡C—, —CR=CR—, —CR=CR—CR=CR—, —CR=N—, —N=CR—, and —N=N—, wherein R is as defined hereinabove.

15. The process of claim 13, wherein Y is selected from the group consisting of $NO_2$, $SO_2R$, $SO_2CH_2F$, $SO_2CHF_2$, $S(NSO_2CF_3)CF_3$, $CF_3$, $CO_2R$, $COCF_3$, cyano, cyanovinyl, dicyanovinyl, and tricyanovinyl, wherein R is a hydrogen or a $C_1$ to $C_{20}$ hydrocarbyl group.

16. The process of claim 10, 11 or 12 wherein A at each occurrence is independently selected from the group consisting of:

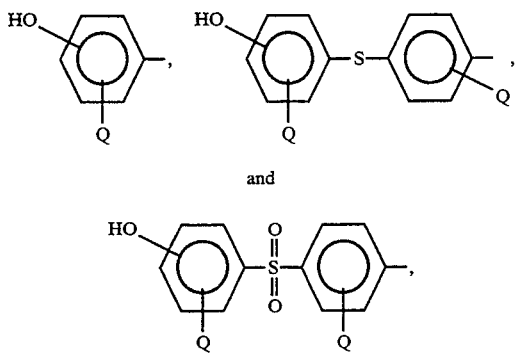

and

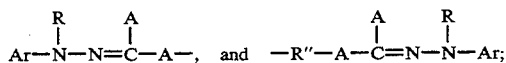

wherein Q is selected from the group consisting of hydrogen, OR', R, RO, RS, R₂N, $$\underset{Ar-N-N=C-A-}{\overset{R\quad A}{|\quad |}}, \quad \text{and} \quad \underset{-R''-A-C=N-N-Ar;}{\overset{A\quad R}{|\quad |}}$$

where A, R', R and Ar are as previously defined, and R'' is a divalent substituted or unsubstituted hydrocarbyl group containing 1 to 20 carbon atoms.

17. The process of claim 11 or 12, wherein compound of Formula (I) is a diglycidylether of Bis (N'-methyl-4-nitrophenylhydrazone) of 5,5'-methylene-bis-salicylaldehyde.

18. The process of claims 10, 11 or 12, wherein the curing agent is selected from the group consisting of 4,4'-diaminodiphenyl sulfone, p-nitroaniline, nitrobenzyl amine, 4-(4-nitrophenylazo)aniline, methyl nitroaniline, amino nitropyrimidine, 2-6-diamine 4-nitrotoluene, 5-nitrobenzotriazole and combinations thereof, bisphenol A, tetrabromobisphenol A, phenolformaldehyde novolac resins, halogenated phenolformaldehyde resins, hydrocarbonphenol resins and combinations thereof.

19. A device comprising the composition of claims 1 or 2.

20. The composition of claim 7, wherein the condensation polymerizable monomer is diglycidyl ether of bisphenol A.

21. The composition of claim 8, wherein the condensation polymerizable monomer is 9,9-bis(4-hydroxyphenyl) fluorene.

22. The process of claim 10, wherein the epoxy composition is the reaction product of 9,9-bis-(4-hydroxyphenyl) fluorene and digylcidyl ether of bis(N'-methyl-4-nitrophenylhydrazone) of 5,5'-methylene-bis-salicyladehyde.

* * * * *

UNITED STATES PATENT AND TRADEMARK OFFICE
CERTIFICATE OF CORRECTION

PATENT NO. : 5,445,854
DATED : August 29, 1995
INVENTOR(S) : Mark D. Newsham; Muthiah N. Inbasekaran; Michael N. Mang It is certified that error appears in the above-indentified patent and that said Letters Patent is hereby corrected as shown below:

On the title page, item [21], Application number 329,374 should read --159,074--.

Col. 14, line 35, "areas" should read -- are as--.
Col. 15, line 39, "$C_{6+}$" should read --$C_{6-30}$--.

Signed and Sealed this

Twenty-third Day of July, 1996

Attest:

BRUCE LEHMAN

Attesting Officer     Commissioner of Patents and Trademarks